United States Patent [19]

Sohn et al.

[11] Patent Number: 5,037,468
[45] Date of Patent: Aug. 6, 1991

[54] PYRAZOLINES AND THEIR USE AS SAFENERS

[75] Inventors: Erich Sohn, Esslingen; Wolfgang Rösch, Gersthofen; Klaus Bauer, Hanau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 553,865

[22] Filed: Jul. 16, 1990

[30] Foreign Application Priority Data

Jul. 18, 1989 [DE] Fed. Rep. of Germany ....... 3923649

[51] Int. Cl.$^5$ .................... A01N 43/48; C07D 231/10
[52] U.S. Cl. .......................................... 71/92; 548/377
[58] Field of Search ............................ 548/377; 71/92

[56] References Cited

PUBLICATIONS

Chemical Abstracts, 85:143027e, 1,3-Dipolar Cycloaddition to Unsaturated Compounds, Reaction of 2-Methoxy-1,3-Butadiene with Nitrylimines, Kheruze et al., Zh. Org. Khim., 1976, 12(6), 1332–7.

Chemical Abstracts, 94:208035p, Regioselectivity in Reactions Involving Addition to 2-Methoxy-3-Methyl-1,3-Butadiene, Kobesheva et al., Zh. Org. Khim., 1981, 17(2), 260–8.

Chemical Abstracts, 101:38399d, The Reaction of N-aryl-C-(ethoxycarbonyl)nitrilimine with Olefins, Shimizu et al., Bull. Chem. Soc. Jpn., 1984, 57(3), 787–90.

*Primary Examiner*—Mary C. Lee
*Assistant Examiner*—Joseph K. McKane
*Attorney, Agent, or Firm*—Curtis, Morris & Safford

[57] ABSTRACT

Compounds of the formula (I)

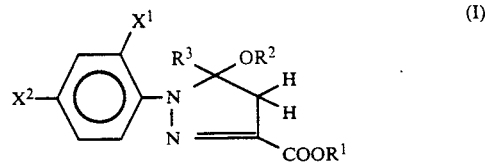

where
$X^1$ and $X^2$ independently of one another are halogen or haloalkyl,
$R^1$ is hydrogen, alkyl or alkoxyalkyl,
$R^2$ is alkyl or haloalkyl, and
$R^3$ is hydrogen, alkyl, alkenyl or alkynyl, can reduce, or entirely compensate, phytotoxic secondary effects of herbicides on crop plants and are therefore suitable as agents for the selective use of herbicides.

4 Claims, No Drawings

PYRAZOLINES AND THEIR USE AS SAFENERS

When plant treatment agents, in particular herbicides, are applied, it is possible that undesired damage occurs on the crop plants, which cannot be tolerated. In particular when herbicides are applied after the crop plants have emerged, it is therefore often desired to avoid the risk of a potential phytotoxicity.

Compounds which have the properties of protecting crop plants against phytotoxic damage by herbicides without adversely affecting the actual herbicidal action in these agents are called "antidotes" or "safeners".

Various compounds have already been described for this application; cf., for example, EP-A 152,006 (=US-A-4,602,932) and EP-A 0,174,562 (=US-A-4,639,266).

1-Phenyl- and 1-(pyrid-2-yl)-pyrazole derivatives were suggested as safeners in German Patent Application P-3 808 896.7 (EP-A 0,333,131).

Only few 1-aryl-4,5-pyrazoline-3-carboxylic acid derivatives have been disclosed. For example, Kheraze and coworkers (Zh. Org. Khim. 12 (1976) 6, 1332-1337 and Zh. Org. Khim. 14 (1978) 1396-1401) describe pyrazolines of the formulae

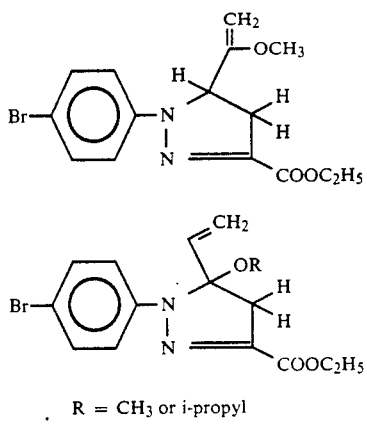

R = CH₃ or i-propyl

A biological action of these alkoxypyrazolines has hitherto not been described.

A present invention relates to 4,5-pyrazoline-3-carboxylic acid derivatives of the formula (I)

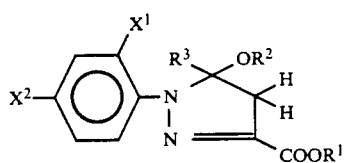

where
$X^1$ and $X^2$ independently of one another are halogen or haloalkyl,
$R^1$ is hydrogen, alkyl or alkyloxyalkyl,
$R^2$ is alkyl or haloalkyl, and
$R^3$ is hydrogen, alkyl, alkenyl or alkynyl.

Formula (I) in this context comprises all geometric isomers and stereoisomers which are possible. Furthermore, halogen in formula (I) denotes fluorine, chlorine, bromine or iodine, alkyl denotes straight-chain, branched or cyclic alkyl, alkenyl denotes straight-chain or branched alkenyl, it being possible for the double bond to be in any desired position in the alkenyl radical, and alkynyl denotes straight-chain or branched alkynyl, it being possible in this case too for the triple bond to be located anywhere in the alkynyl radical, and haloalkyl denotes alkyl which is monosubstituted or polysubstituted by halogen.

Compounds of the formula (I) according to the invention where
$X^1$ and $X^2$ independently of one another are halogen or $C_1$-$C_4$-haloalkyl,
$R^1$ is $C_1$-$C_6$-alkyl, $C_3$-$C_6$-cycloalkyl or ($C_1$-$C_6$-alkyloxy)-$C_1$-$C_6$-alkyl,
$R^2$ is $C_1$-$C_6$-alkyl, $C_3$-$C_6$-cycloalkyl or $C_1$-$C_6$-haloalkyl, and
$R^3$ is hydrogen, $C_1$-$C_6$-alkyl, $C_3$-$C_6$-cycloalkyl, $C_2$-$C_6$-alkenyl or $C_2$-$C_6$-alkynyl, are of particular interest.

Haloalkyl is preferably trifluoromethyl, 2-chloroethyl, 1,1,2,2-tetrafluoroethyl or hexafluoropropyl, and halogen is preferably fluorine, chlorine or bromine. Alkyl preferably represents one of the radicals methyl, ethyl, n-propyl, i-propyl, the butyl, pentyl and hexyl isomers, cyclopentyl and cyclohexyl. Alkenyl is preferably one of the radicals vinyl, 1-propen-1-yl, 1-propen-2-yl, and the butenyl, pentenyl and hexenyl isomers. Alkynyl preferably represents acetylenyl, 1-propynyl or 2-propynyl.

Compounds of the formula (I) according to the invention where
$X^1$ and $X^2$ independently of one another are fluorine, chlorine, bromine or trifluoromethyl,
$R^1$ is $C_1$-$C_4$-alkyl or ($C_1$-$C_4$-alkyloxy)-$C_1$-$C_4$-alkyl,
$R^2$ is $C_1$-$C_4$-alkyl which is unsubstituted or monosubstituted or polysubstituted by halogen, and
$R^3$ is hydrogen, $C_1$-$C_4$-alkyl, $C_2$-$C_4$-alkenyl or $C_2$-$C_4$-alkynyl, are particularly preferred.

The invention furthermore relates to a process for the preparation of the compounds of the formula (I), which comprises reacting a compound of the formula (II)

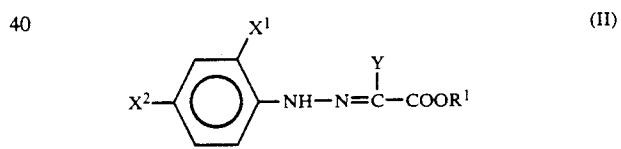

where Y is chlorine or bromine and $X^1$, $X^2$ and $R^1$ have the abovementioned meanings, with enol ethers of the formula (III)

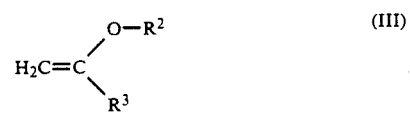

where $R^2$ and $R^3$ have the abovementioned meanings.

The components can be employed in equimolar amounts or in excess of the compounds of the formula (III), usually in the molar ratio (II):(III) of 1:1.05 to 1:20, preferably in the molar ratio of 1:1.1 to 1:5.

Some of the compounds of the formula (II) are known or can be synthesized by customary processes. For example, they can be obtained from the corresponding anilines by diazotization and coupling with the corresponding 2-chloroacetic esters. The compounds of the formula (III) are likewise accessible by customary processes, for example by eliminating alcohol from the corresponding ketals.

In general, the reaction is carried out at between 0° and 150° C., advantageously between 20° and 100° C., if appropriate in the presence of an organic base such as sterically hindered amines, for example triethylamine or pyridine, or of an inorganic base such as, for example, potassium carbonate, potassium hydroxide or sodium carbonate, with or without the presence of an organic solvent such as, if appropriate, a halogenated aliphatic or aromatic hydrocarbon or an ether, for example the solvent toluene, xylene, dichloroethane, dimethoxyethane, diglyme or triglyme, cyclohexane, petroleum ether or chlorobenzene. Bases and solvents are only enumerated by way of example, without the process being limited to these examples.

By alcohol elimination, the compounds of the formula (I) can be converted into corresponding pyrazole esters, as are described as safeners in German Patent Application P 3,808,896.7 (EP-A-0,333,131).

The invention therefore furthermore relates to a process for converting the compounds of the formula (I) into the corresponding pyrazoles, which comprises treating the compounds of the formula (I) without or in the presence of an organic solvent such as, for example, an optionally halogenated aliphatic or aromatic hydrocarbon or an ether, for example the solvent toluene, xylene, chlorobenzene, diglyme or triglyme, if appropriate in the presence of an inorganic or organic acid such as mineral acids or organic sulfonic acids, for example the acids p-toluenesulfonic acid, phosphoric acid, sulfuric acid or trifluoromethanesulfonic acid, at temperatures between 0° and 200° C., advantageously between 50° and 120° C., with the elimination of the compound of the formula $HOR^2$ where $R^2$ is as defined in formula (I).

The compounds of the formula (I) have the property of reducing or completely preventing phytotoxic secondary effects of plant protection agents, in particular of herbicides, which can occur when these agents are employed in crops. The compounds of the formula (I) are capable of substantially or completely compensating harmful secondary effects of the herbicides, without impairing the effectiveness of these herbicides against harmful plants. It is possible to considerably enlarge the field of application of conventional herbicides by adding the safener compound of the formula (I).

The present invention therefore also relates to a method of protecting crop plants against phytotoxic secondary effects of plant protection agents, in particular herbicides, which comprises treating the plants, seeds of the plants or areas under cultivation with a compound of the formula (I) before, after, or simultaneously with the plant protection agent.

Examples of herbicides whose phytotoxic secondary effects can be reduced by means of the compounds of the formula (I) are carbamates, thiocarbamates, haloacetanilides, substituted phenoxy-, naphthoxy- and phenoxyphenoxycarboxylic acid derivatives as well as heteroaryloxyphenoxycarboxylic acid derivatives, such as quinolyloxy-, quinoxalyloxy-, pyridyloxy-, benzoxazolyloxy- and benzothiazolyloxy-phenoxycarboxylic acid esters, and furthermore dimedone oxime derivatives. Preferred compounds amongst these are phenoxyphenoxy- and heteroaryl-oxyphenoxy-carboxylic acid esters and structural analogs such as benzylphenoxycarboxylic acid esters. Suitable esters in this connection are, in particular, lower alkyl, alkenyl and alkynyl esters.

The following herbicides may be mentioned by way of example but without imposing any restriction:

A) Herbicides of the type of the $(C_1-C_4)$alkyl, $(C_2-C_4)$-alkenyl or $(C_3-C_4)$alkynyl phenoxyphenoxy- and heteroaryl-oxyphenoxy-carboxylates, such as methyl 2-(4-(2,4-dichlorophenoxy)phenoxy)propionate, methyl 2-(4-(4-bromo-2-chlorophenoxy)phenoxy)propionate, methyl 2-(4-(4-trifluoromethylphenoxy)phenoxy)propionate, methyl 2-(4-(2-chloro-4-trifluoromethylphenoxy)phenoxy)propionate, methyl 2-(4-(2,4-dichlorobenzyl)phenoxy)propionate, 2-isopropylideneaminooxyethyl (R)-2-[4-(6-chloroquinoxalin-2-yloxy)phenoxy]propionate (propaquizafop), ethyl 4-(4-(4-trifluoromethylphenoxy)phenoxy)pent-2-enoate, ethy 2-(4-(3,5-dichloropyridyl-2-oxy)phenoxy)propionate, propargyl 2-(4-(3,5-dichloropyridyl-2-oxy)phenoxy)propionate, ethyl 2-(4-(6-chlorobenzoxazol-2-yloxy)phenoxy)propionate, ethyl 2-(4-(6-chlorobenzothiazol-2-yloxy)phenoxy)propionate, methyl 2-(4-(3-chloro-5-trifluoromethyl-2pyridyloxy)phenoxy)propionate, butyl 2-(4-(5-trifluoromethyl-2-pyridyloxy)phenoxy)propionate, ethyl 2-(4-(6-chloro-2-quinoxalyloxy)phenoxy)-propionate, ethyl 2-(4-(6-fluoro-2-quinoxalyloxy)phenoxy)propionate, propargyl 2-(4-(5-chloro-3-fluoropyridyl-2-oxy)phenoxy)propionate, ethyl 2-(4-(6-chloro-2-quinolyloxy)phenoxy)propionate, trimethylsilylmethyl 2-(4-(3,5-dichloropyridyl-2-oxy)phenoxy)propionate, ethyl 2-(4-(3-chloro-5-trifluoromethoxy-2-pyridyloxy)phenoxy)propionate, B) Chloroacetanilide herbicides, such as N-methoxymethyl-2,6-diethyl-chloroacetanilide, 2-chloro-N-(2-ethyl-6-methylphenyl)-N-(2-methoxy-1-methylethyl)acetamide, N-(3-methyl-1,2,4-oxadiazol-5-ylmethyl)-2,6-dimethylchloroacetanilide, C) Thiocarbamates, such as S-ethyl N,N-dipropylthiocarbamate or S-ethyl N,N-diisobutylthiocarbamate, D) Dimedone derivatives, such as 2-(N-ethoxybutyrimidoyl)-5-(2-ethylthiopropyl)-3-hydroxy-2-cyclohexen-1-one, 2-(N-ethoxybutyrimidoyl)-5-(2-phenylthiopropyl)-3-hydroxy-2-cyclohexen-1-one or 2-(1-allyloxyiminobutyl)-4-methoxycarbonyl-5,5-dimethyl-3-oxocyclohexenol, 2-(N-ethoxypropionamidoyl)-5-mesityl-3-hydroxy-2-cyclohexen-1-one (also called 5-(2,4,6-trimethylphenyl)-3-hydroxy-2-[1-(ethoxyimino)propyl]cyclohex-2-en-1-one), 2-(N-ethoxybutyrimidoyl)-3-hydroxy-5-(thian-3-yl)-2-cyclohexen-1-one, 2-[1-(ethoxyimino)butyl]-3-hydroxy-5-(2H-tetrahydrothiopyran-3-yl)-2-cyclohexen-1-one (BASF 517); (±)-2-[(E)-3-chloroallyloxyiminopropyl]-5-(2-ethylthiopropyl)-3-hydroxycyclohex-2-enone (clethodim).

Preferred herbicides which may be mentioned from amongst those which can be combined according to the invention with the compounds of the formula (I) are the compounds listed under A), in particular ethyl 2-(4-(6-chlorobenzoxazol-2-yloxy)phenoxy)propionate, ethyl 2-(4-(6-chlorobenzothiazol-2-yloxy)phenoxy)propionate and propargyl 2-(4-(5-chloro-3-fluoropyridyl-2-oxy)phenoxy)-propionate. From the substances mentioned under D), 2-(N-ethoxypropionamidoyl)-5-mesityl-3-hydroxy-2-cyclohexen-1-one is particularly important.

The ratio by weight of safener (compound I): herbicide can vary within wide limits and is preferably in the range from 1:10 to 10:1, in particular 2:1 to 1:10.

The amounts of herbicide and safener which are ideal in each case depend on the type of the herbicide used or on the safener used as well as on the nature of the plant canopy to be treated, and they can be determined for each individual case by appropriate experiments.

The safeners are mainly employed in particular in cereal crops (wheat, rye, barley, oats), rice, maize and sorghum, but also in cotton, sugar beet, sugar cane and soya bean.

Depending on their properties, the safeners can be used for pre-treating the seed of the crop plant (seed treatment), or they can be incorporated in the seed furrows prior to sowing, or used together with the herbicide prior to, or after, plant emergence. Pre-emergence treatment includes both the treatment of the area under cultivation prior to sowing and treatment of the areas under cultivation where seed has been sown but growth of the crop plants has not yet taken place.

However, application of the antidote simultaneously with the herbicide in the form of tank mixes or ready-mixes is preferred.

The compounds of the formula (I) or their combinations with one or more of the herbicides or groups of herbicides mentioned can be formulated in a variety of ways, as predetermined by the biological and/or chemophysical parameters. The following possibilities are therefore suitable for formulation: wettable powders (WP), emulsifiable concentrates (EC), aqueous solutions (SL), concentrated emulsions (EW), such as oil-in-water and water-in-oil emulsions, sprayable solutions or emulsions, dispersions on an oil or water base (SC), dusting agents (DP), seed treatment agents, granules in the form of microgranules, spray granules, coated granules and adsorption granules, soil granules and granules for scattering, water-dispersible granules (WG), ULV formulations, microcapsules or waxes.

These individual formulation types are known in principle and are described, for example, in: Winnacker-Küchler, "Chemische Technologie [Chemical Technology]", Volume 7, C. Hauser Verlag, Munich, 4th Ed., 1986; van Valkenburg, "Pesticides Formulations", Marcel Dekker N.Y., 2nd Ed. 1972-73; K. Martens, "Spray Drying Handbook", 3rd Ed. 1979, G. Goodwin Ltd., London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldewell NJ; H.v. Olphen, "Introduction to Clay Colloid Chemistry", 2nd Ed., J. Wiley & Sons, NY 1950; McCutcheon's, "Detergents and Emulsifiers Annual", MC Publ. Corp., Ridgewood NJ; Sisley and Wood, "Encyclopedia of Surface Active Agents", Chem. Publ. Co. Inc., NY 1964; Schönfeldt, "Grenzflächenaktive Äthylenoxidaddukte" [Surface-active Ethylene Oxide Adducts], Wiss. Verlagsgesellschaft, Stuttgart 1976; Winnacker-Küchler, "Chemische Technologie [Chemical Technology]", Volume 7, C. Hauser Verlag Munich, 4th Ed. 1986.

The invention therefore also relates to the agents which contain the compounds of the formula (I) according to the invention. These are mainly, on the one hand, plant-protecting agents which contain one or more compounds of the formula (I) and customary inert auxiliaries which are appropriate for the particular type of formulation, and, on the other hand, herbicidal agents which contain a combination of compounds of the formula (I) and one or more heriicides and customary auxiliaries which are appropriate for the particular type of formulation.

Combinations with other pesticidally active substances, fertilizers and/or growth regulators may also be prepared on the basis of these formulations, for example in the form of readymix or as a tank mix.

Wettable powders are preparations which are uniformly dispersible in water and which, besides the active substance, also contain wetting agents, for example polyoxethylated alkylphenols, polyoxethylated fatty alcohols and fatty amines, alkanesulfonates or alkylarylsulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of alkylarylsulfonic acids, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products (for example block polymers), alkyl polyethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophillite, or diatomaceous earth.

Granules can be produced either by spraying the active substance onto adsorptive, granulated inert material or by applying active substance concentrates onto the surface of carriers, such as sand, kaolinites or of granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the formulations according to the invention contain 0.1 to 99 % by weight, preferably 1 to 95 % by weight, in particular 2 to 90 % by weight, of active substance, i.e. active substance of the formula (I) or a combination of the activesubstance of the formula (I) with a herbicide.

The concentration of active substance in wettable powders is, for example, about 10 to 90 % by weight, the remainder to 100 % by weight is composed of conventional formulation components. In the case of emulsifiable concentrates, the concentration of active substance can be about 1 to 80 % by weight, preferably 5 to 80 % by weight. Formulations in the form of dusts mostly contain 1 to 30 % by weight, preferably 5 to 20 % by weight, of active substance, sprayable solutions about 0.2 to 25 % by weight, preferably 2 to 20 % by weight. In the case of granules, the active substance content depends partly on whether the active compound is liquid or solid and on which granulation auxiliaries, fillers etc. are used. In the case of water-dispersible granules, the active substance content is generally between 10 and 90 % by weight.

In addition, the active substance formulations mentioned contain, if appropriate, the adhesives, wetting agents, dispersing agents, emulsifiers, penetrants, solvents, fillers or carriers which are conventional in each case.

For use, the concentrates, present in commercially available form, are diluted, if appropriate, in a customary manner, for example using water in the case of wettable powders, emulsifiable concentrates, dispersions and in some cases also in the case of microgranules. Preparations in the form of dusts or granulated preparations and also sprayable solutions are usually not further diluted with other inert substances before use.

The application rate required for the compounds of the formula (I) varies with the external conditions, such as, inter alia, temperature, humidity, and the nature of the herbicide used. It can vary within wide limits, for example between 0.005 and 10.0 kg/ha or more of active ingredient, preferably, however, it is between 0.01 and 5 kg/ha.

The examples which follow serve to illustrate the invention in greater detail:

A. FORMULATION EXAMPLES a) A dusting agent is obtained by mixing 10 parts by weight of a compound of the formula (I) or, if appropriate, a mixture of an active substance with a herbicide, and 90 parts by weight of talc as inert substance and comminuting the mixture in a hammer mill.

b) A wettable powder which is readily dispersible in water is obtained by mixing 25 parts by weight of a compound of the formula (I) or a mixture of (I) with a herbicide, 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk-mill.

c) A dispersion concentrate which is readily dispersible in water is obtained by mixing 20 parts by weight of a compound of the formula (I) or a mixture of (I) with a herbicide with 6 parts by weight of alkylphenol polyglycol ether (®Triton X 207), 3 parts by weight of isotridecanol polyglycol ether (8 EO=8 ethylene oxide units) and 71 parts by weight of paraffinic mineral oil (boiling range, for example, about 255° to above 277° C), and grinding the mixture in a ball mill to a fineness of below 5 microns.

d) An emulsifiable concentrate is obtained from 15 parts by weight of a compound of the formula (I) or a mixture of (I) and a herbicide, 75 parts by weight of cyclohexanone as the solvent and 10 parts by weight of oxethylated nonylphenol as the emulsifier.

e) A concentrate of a phenoxycarboxylic acid ester and an antidote (10:1) which is readily emulsifiable in water is obtained from
12.00% by weight of ethyl 2-[4-(6-chlorobenzoxazol-2-yloxy)phenoxy]propionate,
1.20% by weight of compound of the formula (I),
69.00% by weight of xylene,
7.80% by weight of calcium dodecylbenzenesulfonate,
6.00% by weight of ethoxylated nonylphenol (10 EO)
4.00% by weight of ethoxylated castor oil (40 EO)
The preparation is carried out as indicated for Example a).

f) A concentrate of a phenoxycarboxylic acid ester and an antidote (1:10) which is readily emulsifiable in water is obtained from
4.0% by weight of ethyl 2-[4-(6-chlorobenzoxazol-2-yloxy)phenoxy]propionate,
40.0% by weight of compound of the formula (I)
30.0% by weight of xylene,
20.0% by weight of cyclohexanone,
4.0% by weight of calcium dodecylbenzenesulfonate,
2.0% by weight of ethoxylated castor oil (40 EO).

B. PREPARATION EXAMPLES

Example 1

Ethyl 1-(2,4-dichlorophenyl)-5-isopropyl-5-methoxypyrazoline-3-carboxylate 10 g of 2-methoxy-3-methylbut-1-ene and 10 g of triethylamine are heated at 80° C. 15.5 g of the 2,4-dichlorophenylhydrazone of ethyl 2-chloroglyoxalate (formula (II) with $X^1=X^2=Y=Cl$, $R^1=C_2H_5$) (IIa) in 50 ml of toluene are added dropwise to this mixture within half an hour. Stirring is continued for 4 hours at 80° C., the mixture is cooled, the precipitate is then filtered off with suction and the filtrate is concentrated in vacuo under mild conditions. After column chromatography (diluent petroleum ether/ethyl acetate 1:0 -- >1:5) over silica gels 8.3 g of pyrazoline are obtained as an oil.

EXAMPLE 2

Ethyl 1-(2,4-dichlorophenyl)-5-ethoxy-5-isopropyl-pyrazoline-3-carboxylate 6.2 g of 2-ethoxy-3-methylbut-1-ene and 6 g of triethylamine are initially introduced into 20 ml of cyclohexane at 70° C.; 15.0 g of compound (IIa) from Example 1 in 150 ml of cyclohexane are added dropwise over 1/2 hour. After 10 hours at this temperature, the precipitate is filtered off with suction and the filtrate is concentrated in vacuo. A precipitate of the product (9.2 g) of melting point 105°–110° C. is obtained as a solid from the mother liquor.

EXAMPLE 3

Ethyl 1-(2,4-dichlorophenyl)-5-methoxy-5-t-butyl-pyrazoline-3-carboxylate 22.8 g of 3,3-dimethyl-2-methoxybut-1-ene, 15 g of potassium carbonate and 20 ml of dimethoxyethane are heated at 80° C; 15 g of compound (IIa) from Example 1 in 100 ml of toluene are added dropwise at the same temperature over 1/2 hour. After stirring has been continued for 15 hours, the precipitate is filtered off with suction, the filtrate is concentrated in vacuo under mild conditions and the product is chromatographed as in Example 1. 10.7 g of product of melting point 130°–133° C. are obtained.

The examples from Table I can be prepared analogously.

TABLE I

| | Alkoxypyrazolines of the formula (I) | | | | |
|---|---|---|---|---|---|
| Example No. | $X^1, X^2$ | $R^1$ | $R^2$ | $R^3$ | M.p. [°C.] $n_D^{20}$ |
| 4 | 2,4-Cl$_2$ | C$_2$H$_5$ | n-C$_4$H$_9$ | H | oil |
| 5 | " | CH$_3$ | CH$_3$ | i-C$_3$H$_7$ | |
| 6 | " | (CH$_2$)$_2$OCH$_3$ | CH$_3$ | i-C$_3$H$_7$ | 76–78 |
| 7 | " | C$_2$H$_5$ | CH$_3$ | C$_2$H$_3$ | |

TABLE I-continued

Alkoxypyrazolines of the formula (I)

| Example No. | $X^1, X^2$ | $R^1$ | $R^2$ | $R^3$ | M.p. [°C.] $n_D^{20}$ |
|---|---|---|---|---|---|
| 8 | " | $C_2H_5$ | $CH_3$ | $C_2H$ | resin |
| 9 | 4-Cl-2-$CF_3$ | $C_2H_5$ | $CH_3$ | i-$C_3H_7$ | resin |
| 10 | 2,4-$Br_2$ | $C_2H_5$ | $CH_3$ | i-$C_3H_7$ | 1,5478 |
| 11 | 2-Cl-4-$CF_3$ | $C_2H_5$ | $CH_3$ | i-$C_3H_7$ | |
| 12 | 2,4-$Cl_2$ | $C_2H_5$ | $CH_3$ | $CH_3$ | |
| 13 | 2,4-$Cl_2$ | n-$C_3H_7$ | $C_2H_5$ | H | |
| 14 | " | n-$C_4H_9$ | $CH_3$ | H | |
| 15 | " | n-$C_5H_{11}$ | $CH_3$ | $CH_3$ | |
| 16 | " | i-$C_6H_{13}$ | i-$C_3H_7$ | H | |
| 17 | " | cyclohexyl | $CH_3$ | i-$C_3H_7$ | |
| 18 | " | cyclopentyl | $CH_3$ | vinyl | |
| 19 | " | $CH_3$ | n-$C_5H_{11}$ | —C≡CH | |
| 20 | " | $CH_3$ | i-$C_6H_{13}$ | —C≡CH | |
| 21 | " | $(CH_2)_3OCH_3$ | $CH_3$ | $C_2H_5$ | |
| 22 | " | $(CH_2)_2OC_2H_5$ | $C_2H_5$ | $C_2H_5$ | |
| 23 | 2,4-$(CF_3)_2$ | $CH_3$ | $CH_3$ | $CH_3$ | |
| 24 | " | $C_2H_5$ | $CH_3$ | $CH_3$ | |
| 25 | " | $C_2H_5$ | $CH_3$ | i-$C_3H_7$ | |
| 26 | 2,4-$F_2$ | $CH_3$ | $CH_3$ | H | |
| 27 | 2-F-4-Cl | $CH_3$ | $CH_3$ | H | |
| 28 | 2-F-4-$CF_3$ | $C_2H_5$ | $C_2H_5$ | H | |
| 29 | 2,4-$Br_2$ | $(CH_2)_2$—$OCH_3$ | $CH_3$ | vinyl | |
| 30 | 4-Cl-2-$CF_3$ | $CH_3$ | $C_2H_5$ | H | |
| 31 | 2,4-$Cl_2$ | $CH_3$ | $CH_3$ | cyclohexyl | |
| 32 | " | $C_2H_5$ | $CH_3$ | cyclopentyl | |
| 33 | " | $CH_3$ | $C_2H_5$ | vinyl | |
| 34 | " | $C_2H_3$ | 2-Cl$C_2H_4$ | H | |
| 35 | " | $C_2H_5$ | 2-Cl$C_2H_4$ | H | |
| 36 | " | $C_2H_5$ | 3-H—$C_3F_6$ | H | |

C. EXAMPLES OF CONVERSIONS INTO PYRAZOLES

Example 1

Ethyl 1-(2,4-dichlorophenyl)-5-isopropylpyrazole-3-carboxylate 10 g of pyrazoline from Example B.1 are kept at 100° C. for 2 hours and recrystallized from a little petroleum ether. 6.3 g of product having a melting point of 93°–95° C. are obtained as a solid (see note at the end of Example 2).

Example 2

10 g of crude product from Example B.1 (prior to column chromatography) are taken up in 150 ml of anhydrous toluene, and the mixture is refluxed with 0.5 g of p-toluenesulfonic acid for 4 hours. It is concentrated in vacuo and the product is recrystallized from a little petroleum ether. Yield 6.1 g, m.p. 93°–95° C. (note: the lower melting point of 70°–77° C. which is indicated in P 3 808 896.7, Example 302, can be attributed to contamination with the isomeric pyrazole-3 ester.)

D. BIOLOGICAL EXAMPLES

Example 1

In the greenhouse, wheat and barley were grown in plastic pots up to the 3- to 4-leaf stage and then reated postemergence with the safener compounds and the tested herbicides. In these examples, the herbicides and the compounds of the formula (I) were applied in the form of aqueous suspensions or emulsions, and an amount of 800 1 of water/ha (converted) was used. 3 to 4 weeks after the treatment, the plants were scored visually for any type of damage by the herbicides applied, the extent of longterm growth inhibition being taken into account, in particular. The degree of damage or of safener action of compounds of the formula (I), by themselves or in combination with herbicides, was determined in % damage.

The results show (cf. Table II) that the compounds according to the invention can effectively reduce extensive herbicide damage on crop plants.

Even in the case of massive overdoses of a herbicide such as fenoxaprop-ethyl, extensive damage of the crop plants is markedly reduced, and lesser damage is compensated completely. Mixtures of herbicides and compounds according to the invention are therefore suitable in an advantageous manner for selectively combating weeds in cereal crops.

TABLE II

| Active ingredient/ mixture of a.i. | Safener action Dose [kg of a.i./ha] | Herbicidal action in % TRAE | HOVU |
|---|---|---|---|
| H | 2.0 | 75 | — |
|   | 0.2 | — | 80 |
| H + Ex. 1 | 2.0 + 1.0 | 10 | — |
|   | 2.0 + 0.25 | 10 | — |
|   | 0.2 + 1.0 | — | 5 |
|   | 0.2 + 0.25 | — | 10 |
| H + Ex. 10 | 0.2 + 1.25 | — | 17 |

Abbreviations:
H = herbicide fenoxaprop-ethyl
Ex. No. = see Example from Table I
TRAE = *Triticum aestivum* (soft wheat)
HOVU = *Hordeum vulgare* (barley)

We claim:
1. A compound of the formula (I)

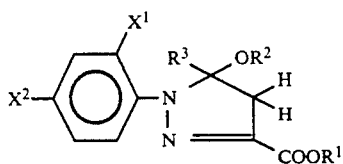

(I)

where

X$^1$ and X$^2$ independently of one another are halogen or haloalkyl,

R$^1$ is hydrogen, alkyl or alkyloxyalkyl,

R$^2$ is alkyl or haloalkyl and

R$^3$ is hydrogen, alkyl, alkenyl or alkynyl.

2. A compound of the formula (I) as claimed in claim 1, wherein

X$^1$ and X$^2$ independently of one another are halogen or C$_1$–C$_4$-haloalkyl, R$^1$ is C$_1$–C$_6$-alkyl, C$_3$–C$_6$-cycloalkyl or (C$_1$–C$_6$-alkyloxy)C$_1$–C$_6$-alkyl, R$^2$ is C$_1$–C$_6$-alkyl, C$_3$–C$_6$-cycloalkyl or C$_1$–C$_6$-haloalkyl and R$^3$ is hydrogen, C$_1$–C$_6$-alkyl, C$_3$–C$_6$-cycloalkyl, C$_2$–C$_6$-alkenyl or C$_2$–C$_6$-alkynyl.

3. A compound as claimed in claim 1, wherein X$^1$ and X$^2$ independently of one another are fluorine, chlorine, bromine or trifluoromethyl, R$^1$ is C$_1$–C$_4$-alkyl or (C$_1$–C$_4$-alkyloxy)-C$_1$–C$_4$-alkyl, R$^2$ is C$_1$–C$_4$-alkyl which is unsubstituted or monosubstituted or polysubstituted by halogen, and R$^3$ is hydrogen, C$_1$–C$_4$-alkyl, C$_2$–C$_4$-alkenyl or C$_2$–C$_4$-alkynyl.

4. A plant-protecting agent which contains a compound of the formula (I), as claimed in claim 1, and inert carriers or other customary formulation auxiliaries.

* * * * *